(12) United States Patent
Smith, III (10) Patent No.: US 11,179,301 B2
(45) Date of Patent: Nov. 23, 2021

(54) SKIN CLEANSING COMPOSITIONS AND METHODS

(71) Applicant: The Procter & Gamble Company, Cincinnati, OH (US)

(72) Inventor: Edward Dewey Smith, III, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 15/787,832

(22) Filed: Oct. 19, 2017

(65) Prior Publication Data

US 2018/0110697 A1    Apr. 26, 2018

Related U.S. Application Data

(60) Provisional application No. 62/410,883, filed on Oct. 21, 2016.

(51) Int. Cl.

| | | |
|---|---|---|
| *A61K 8/00* | (2006.01) | |
| *A61K 8/06* | (2006.01) | |
| *A61K 8/44* | (2006.01) | |
| *A61Q 13/00* | (2006.01) | |
| *A61K 8/04* | (2006.01) | |
| *A61K 8/34* | (2006.01) | |
| *A61K 8/42* | (2006.01) | |
| *A61K 8/46* | (2006.01) | |
| *A61Q 19/10* | (2006.01) | |

(52) U.S. Cl.
CPC .............. *A61K 8/068* (2013.01); *A61K 8/042* (2013.01); *A61K 8/345* (2013.01); *A61K 8/42* (2013.01); *A61K 8/44* (2013.01); *A61K 8/463* (2013.01); *A61Q 13/00* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 2,438,091 | A | 3/1948 | Lynch |
| 2,528,378 | A | 10/1950 | McCabe, Jr. |
| 2,658,072 | A | 11/1953 | Kosmin |
| 2,758,072 | A | 8/1956 | Sutherland |
| 3,962,150 | A | 6/1976 | Viola |
| 4,728,006 | A | 3/1988 | Drobish |
| 4,747,977 | A | 5/1988 | Whitehead |
| 4,997,641 | A | 3/1991 | Hartnett |
| 5,104,646 | A | 4/1992 | Bolich, Jr. |

(Continued)

FOREIGN PATENT DOCUMENTS

| | | |
|---|---|---|
| CA | 2110951 A1 | 6/1994 |
| CA | 2196774 A1 | 2/1996 |

(Continued)

OTHER PUBLICATIONS

International Search Report and Written Opinion of the International Searching Authority, PCT/US2017/057354, dated Jan. 5, 2018, 11 pages.

(Continued)

*Primary Examiner* — Necholus Ogden, Jr.
(74) *Attorney, Agent, or Firm* — John G. Powell (57) ABSTRACT

A skin cleansing composition includes surfactant, glycerin, perfume, and water, where at least a portion of the composition is in a lamellar phase.

19 Claims, 3 Drawing Sheets

(56) References Cited

U.S. PATENT DOCUMENTS

| | | |
|---|---|---|
| 5,106,609 A | 4/1992 | Bolich, Jr. |
| 5,106,613 A | 4/1992 | Hartnett |
| 5,252,555 A | 10/1993 | Dartnell |
| 5,308,526 A | 5/1994 | Dias |
| 5,346,639 A | 9/1994 | Hatfield |
| 5,374,614 A | 12/1994 | Behan |
| 5,409,630 A | 4/1995 | Lysy et al. |
| 5,415,857 A | 5/1995 | Robbins |
| 5,449,763 A | 9/1995 | Wulff |
| 5,468,725 A | 11/1995 | Guenin et al. |
| 5,507,970 A | 4/1996 | Ishikawa |
| 5,580,848 A | 12/1996 | Drapier |
| 5,585,343 A | 12/1996 | Mcgee |
| 5,597,792 A | 1/1997 | Klier |
| 5,747,436 A | 5/1998 | Patel et al. |
| 5,804,538 A | 9/1998 | Wei |
| 5,839,614 A | 11/1998 | Brown |
| 5,977,036 A | 11/1999 | Guskey |
| 6,048,834 A | 4/2000 | Drapier et al. |
| 6,074,996 A | 6/2000 | Elliott |
| 6,107,261 A | 8/2000 | Taylor |
| 6,136,771 A | 10/2000 | Taylor |
| 6,204,230 B1 | 3/2001 | Taylor |
| 6,268,330 B1 | 7/2001 | Leonard et al. |
| 6,271,187 B1 | 8/2001 | Hodge |
| 6,303,109 B1 | 10/2001 | Foerster |
| 6,329,331 B1 | 12/2001 | Aronson et al. |
| 6,358,906 B1 | 3/2002 | Ochs |
| 6,362,155 B1 | 3/2002 | Kinscherf |
| 6,405,901 B1 | 6/2002 | Schantz |
| 6,429,177 B1 | 8/2002 | Williams |
| 6,440,907 B1 | 8/2002 | Santora |
| 6,491,933 B2 | 12/2002 | Lorenzi |
| 6,806,249 B2 | 10/2004 | Yang |
| 6,936,578 B2 | 8/2005 | Cordellina |
| 6,977,082 B2 | 12/2005 | Seitz, Jr. |
| 6,998,382 B2 | 2/2006 | Yang |
| 7,094,739 B2 | 8/2006 | Kessler |
| 7,115,535 B1 | 10/2006 | Smith, III |
| 7,608,575 B2 | 10/2009 | Panandiker |
| 7,704,932 B2 | 4/2010 | Evans |
| 7,874,466 B2 | 1/2011 | Mcconville |
| 7,879,780 B2 * | 2/2011 | Tsaur ....................... C11D 1/37 |
| | | 510/130 |
| 7,884,061 B1 | 2/2011 | Hermanson |
| 8,008,239 B2 | 8/2011 | Anantaneni |
| 8,114,826 B1 | 2/2012 | Hermanson |
| 8,207,100 B1 | 6/2012 | Hermanson |
| 8,207,101 B1 | 6/2012 | Yang |
| 8,236,747 B2 | 8/2012 | Holzhauer |
| 8,263,096 B2 | 9/2012 | Myers |
| 8,408,432 B2 | 4/2013 | Delamare |
| 8,461,099 B2 | 6/2013 | Fraser |
| 8,672,195 B2 | 3/2014 | Py |
| 8,697,622 B2 | 4/2014 | Man |
| 8,840,871 B2 | 9/2014 | Wei |
| 8,899,449 B2 | 12/2014 | Daansen |
| 8,937,102 B2 | 1/2015 | Hessel |
| 9,254,498 B2 | 2/2016 | Daansen |
| 9,271,908 B2 * | 3/2016 | Allef ...................... A61K 8/361 |
| 9,849,309 B2 | 12/2017 | Bouzeloc |
| 10,675,231 B2 | 6/2020 | Smyth |
| 10,806,686 B2 | 10/2020 | Smyth |
| 10,952,949 B2 | 3/2021 | Smith, Iii et al. |
| 10,952,950 B2 | 3/2021 | Smith, Iii et al. |
| 2001/0056049 A1 | 12/2001 | Aronson et al. |
| 2002/0034489 A1 | 3/2002 | Wiegland |
| 2003/0180246 A1 | 9/2003 | Frantz |
| 2004/0074924 A1 | 4/2004 | Kuhn |
| 2005/0020468 A1 | 1/2005 | Frantz |
| 2005/0042192 A1 | 2/2005 | Evans |
| 2005/0250658 A1 | 11/2005 | Putman |
| 2006/0035807 A1 | 2/2006 | Kasturi |
| 2006/0078525 A1 | 4/2006 | Tomokuni |
| 2006/0084589 A1 | 4/2006 | Vlad |
| 2006/0183662 A1 | 8/2006 | Crotty et al. |
| 2007/0027050 A1 | 2/2007 | Crotty et al. |
| 2007/0093404 A1 | 4/2007 | Gross |
| 2007/0110700 A1 | 5/2007 | Wells |
| 2007/0114246 A1 | 5/2007 | Awbrey |
| 2007/0289613 A1 | 12/2007 | Geary |
| 2008/0003247 A1 | 1/2008 | Shick |
| 2008/0032909 A1 | 2/2008 | De Buzzaccarini |
| 2008/0118591 A1 | 5/2008 | Natsch |
| 2008/0139434 A1 | 6/2008 | Basappa |
| 2008/0153929 A1 | 6/2008 | Miyahara |
| 2009/0095775 A1 | 4/2009 | Domoy |
| 2009/0155383 A1 | 6/2009 | Kitko |
| 2009/0221463 A1 | 9/2009 | Kitko |
| 2009/0312224 A1 | 12/2009 | Yang |
| 2010/0136175 A1 | 6/2010 | Skiff |
| 2010/0285155 A1 | 11/2010 | Gilbard |
| 2011/0152146 A1 | 6/2011 | Denutte et al. |
| 2011/0152147 A1 | 6/2011 | Smets |
| 2011/0212879 A1 | 9/2011 | Madden |
| 2011/0268778 A1 | 11/2011 | Dihora |
| 2011/0269657 A1 | 11/2011 | Dihora |
| 2011/0269658 A1 | 11/2011 | Dihora |
| 2011/0280823 A1 | 11/2011 | Madden |
| 2011/0281827 A1 | 11/2011 | Tamarkin et al. |
| 2011/0287073 A1 | 11/2011 | Strauss |
| 2012/0015009 A9 | 1/2012 | Taylor |
| 2012/0091218 A1 | 4/2012 | Mikkelsen |
| 2012/0114819 A1 | 5/2012 | Ragnarsson |
| 2012/0208898 A1 | 8/2012 | Dong |
| 2012/0212879 A1 | 8/2012 | Li |
| 2013/0012601 A1 | 1/2013 | Hessel |
| 2013/0029932 A1 | 1/2013 | Kachi |
| 2013/0045306 A1 | 2/2013 | De Cleir |
| 2013/0053295 A1 | 2/2013 | Kinoshita et al. |
| 2013/0075430 A1 | 3/2013 | Ragnarsson |
| 2013/0267451 A1 | 10/2013 | Hardy |
| 2014/0017386 A1 | 1/2014 | Ragnarsson |
| 2014/0162979 A1 * | 6/2014 | Palla-Venkata ........ A61K 8/463 |
| | | 514/63 |
| 2014/0219946 A1 | 8/2014 | Hloucha |
| 2014/0263443 A1 | 9/2014 | Furusawa |
| 2014/0371128 A1 | 12/2014 | Hotz et al. |
| 2015/0057208 A1 | 2/2015 | Frantz |
| 2015/0203799 A1 | 7/2015 | Bettiol et al. |
| 2015/0237905 A1 | 8/2015 | Ragnarsson |
| 2015/0272197 A1 | 10/2015 | Swain |
| 2015/0298875 A1 | 10/2015 | Dagnelie |
| 2015/0322374 A1 | 11/2015 | Tchakalova |
| 2015/0359725 A1 | 12/2015 | Glenn, Jr. |
| 2015/0359726 A1 | 12/2015 | Glenn, Jr. |
| 2015/0359727 A1 | 12/2015 | Glenn, Jr. |
| 2015/0359728 A1 | 12/2015 | Glenn, Jr. |
| 2016/0128917 A1 * | 5/2016 | Wei ........................ A61K 8/416 |
| | | 510/130 |
| 2016/0143821 A1 | 5/2016 | Chang |
| 2016/0167864 A1 | 6/2016 | De Cleir |
| 2016/0309871 A1 | 10/2016 | Torres Rivera et al. |
| 2016/0310369 A1 | 10/2016 | Thompson |
| 2016/0310370 A1 | 10/2016 | Zhao |
| 2016/0310371 A1 | 10/2016 | Zhao |
| 2016/0310372 A1 | 10/2016 | Glenn, Jr. |
| 2016/0310375 A1 | 10/2016 | Torres Rivera |
| 2016/0310376 A1 | 10/2016 | Torres Rivera |
| 2016/0310377 A1 | 10/2016 | Torres Rivera |
| 2016/0310386 A1 | 10/2016 | Smith, III |
| 2016/0310387 A1 | 10/2016 | Smith, III |
| 2016/0310388 A1 | 10/2016 | Smith, III |
| 2016/0310389 A1 | 10/2016 | Thompson |
| 2016/0310390 A1 | 10/2016 | Smith, III |
| 2016/0310391 A1 | 10/2016 | Smith, III |
| 2016/0310392 A1 | 10/2016 | Smith, III |
| 2016/0310393 A1 | 10/2016 | Chang |
| 2016/0310397 A1 | 10/2016 | Johnson |
| 2016/0310402 A1 | 10/2016 | Zhao |
| 2016/0354300 A1 | 12/2016 | Thompson |
| 2016/0374932 A1 | 12/2016 | Song |
| 2017/0087068 A1 | 3/2017 | Callens |
| 2017/0165155 A1 | 6/2017 | Glenn, Jr. |

(56) References Cited

U.S. PATENT DOCUMENTS

| | | |
|---|---|---|
| 2017/0165156 A1 | 6/2017 | Glenn, Jr. |
| 2017/0165157 A1 | 6/2017 | Glenn, Jr. |
| 2017/0165162 A1 | 6/2017 | Glenn, Jr. |
| 2017/0165163 A1 | 6/2017 | Glenn, Jr. |
| 2017/0165164 A1 | 6/2017 | Zhao et al. |
| 2017/0165165 A1 | 6/2017 | Zhao et al. |
| 2017/0165191 A1 | 6/2017 | Glenn, Jr. |
| 2017/0174413 A1 | 6/2017 | Callens |
| 2017/0246101 A1 | 8/2017 | Iwata |
| 2017/0278249 A1 | 9/2017 | Stofel et al. |
| 2017/0304172 A1 | 10/2017 | Chang |
| 2017/0304184 A1 | 10/2017 | Glenn, Jr. |
| 2017/0304185 A1 | 10/2017 | Glenn, Jr. |
| 2017/0304186 A1 | 10/2017 | Glenn, Jr. |
| 2018/0110688 A1 | 4/2018 | Torres Rivera |
| 2018/0110689 A1 | 4/2018 | Torres Rivera |
| 2018/0110690 A1 | 4/2018 | Torres Rivera et al. |
| 2018/0110691 A1 | 4/2018 | Torres Rivera |
| 2018/0110692 A1 | 4/2018 | Torres Rivera |
| 2018/0110693 A1 | 4/2018 | Renock |
| 2018/0110694 A1 | 4/2018 | Renock |
| 2018/0110695 A1 | 4/2018 | Thompson et al. |
| 2018/0110696 A1 | 4/2018 | Johnson |
| 2018/0110704 A1 | 4/2018 | Zhao |
| 2018/0110707 A1 | 4/2018 | Zhao |
| 2018/0110709 A1 | 4/2018 | Smyth |
| 2018/0110710 A1 | 4/2018 | Zhao |
| 2018/0110714 A1 | 4/2018 | Glenn, Jr. |
| 2018/0235861 A1 | 8/2018 | Smyth |
| 2018/0235862 A1 | 8/2018 | Smyth |
| 2020/0253850 A1 | 8/2020 | Smyth |
| 2021/0128434 A1 | 5/2021 | Smith, Iii et al. |

FOREIGN PATENT DOCUMENTS

| | | |
|---|---|---|
| CA | 2631077 C | 3/2015 |
| CN | 1252263 A | 5/2000 |
| CN | 101193619 A | 6/2008 |
| CN | 103893060 A | 7/2014 |
| DE | 4315396 A1 | 11/1994 |
| DE | 19624051 A1 | 12/1997 |
| EP | 0232153 A2 | 8/1987 |
| EP | 0316726 A2 | 5/1989 |
| EP | 0368146 A2 | 5/1990 |
| EP | 0743310 A1 | 11/1996 |
| EP | 0780464 A2 | 6/1997 |
| EP | 1714678 A1 | 10/2006 |
| EP | 1859777 A2 | 11/2007 |
| EP | 2042216 B1 | 9/2015 |
| FR | 2998476 A1 | 5/2014 |
| GB | 2223236 A | 4/1990 |
| GB | 2280682 A | 2/1995 |
| GB | 2284215 A | 5/1995 |
| GB | 2351979 A | 1/2001 |
| GB | 2371307 A | 7/2002 |
| JP | 9194877 A | 7/1997 |
| JP | 1018177 A | 1/1998 |
| JP | 1053795 A | 2/1998 |
| JP | 10182366 A | 7/1998 |
| JP | 2000212031 | 8/2000 |
| JP | 2001213762 A | 8/2001 |
| JP | 200445869 | 12/2004 |
| JP | 3644658 B2 | 5/2005 |
| JP | 2007320884 A | 12/2007 |
| JP | 2010138348 A | 6/2010 |
| JP | 2010150315 A | 7/2010 |
| JP | 2012001597 A | 1/2012 |
| JP | 4915720 B2 | 4/2012 |
| JP | 4965869 B2 | 4/2012 |
| JP | 5465872 B2 | 4/2014 |
| WO | 9418946 A1 | 9/1994 |
| WO | 9612787 A1 | 5/1996 |
| WO | 9616160 A1 | 5/1996 |
| WO | 9730688 A1 | 8/1997 |
| WO | 9748378 A1 | 12/1997 |
| WO | 9806817 A1 | 2/1998 |
| WO | 200062755 A1 | 10/2000 |
| WO | 0076460 A2 | 12/2000 |
| WO | 0137658 A2 | 5/2001 |
| WO | WO0142409 A1 | 6/2001 |
| WO | 02066589 A2 | 8/2002 |
| WO | WO02092050 A2 | 11/2002 |
| WO | 02097020 A2 | 12/2002 |
| WO | 2004045576 A1 | 6/2004 |
| WO | 2008110995 A2 | 9/2008 |
| WO | 2010052070 A2 | 5/2010 |
| WO | 2010052071 A2 | 5/2010 |
| WO | 2010052147 A2 | 5/2010 |
| WO | 2011049932 A1 | 4/2011 |
| WO | 2011094714 A1 | 8/2011 |
| WO | 2012055855 A1 | 5/2012 |
| WO | 2013007473 A2 | 1/2013 |
| WO | 2013163074 A1 | 10/2013 |
| WO | 2014090959 A1 | 6/2014 |
| WO | 2016026777 A1 | 2/2016 |
| WO | 2016077114 A1 | 5/2016 |
| WO | 2016149166 A1 | 9/2016 |
| WO | 2016172468 A1 | 10/2016 |
| WO | 2016172472 A1 | 10/2016 |
| WO | 2016172475 A1 | 10/2016 |
| WO | 2016172478 A1 | 10/2016 |
| WO | 2016172482 A1 | 10/2016 |
| WO | WO2016172405 A1 | 10/2016 |

OTHER PUBLICATIONS

PCT International Search Report and Written Opinion for PCT/US2016/066752 dated Feb. 22, 2017.
All final and non-final office actions for U.S. Appl. No. 15/299,722.
All final and non-final office actions for U.S. Appl. No. 15/435,533.
All final and non-final office actions for U.S. Appl. No. 16/862,666.
All Office Actions, U.S. Appl. No. 15/135,627.
All Office Actions, U.S. Appl. No. 15/135,648.
All Office Actions, U.S. Appl. No. 15/135,659.
All Office Actions, U.S. Appl. No. 15/135,675.
All Office Actions, U.S. Appl. No. 15/135,687.
All Office Actions, U.S. Appl. No. 15/135,697.
Dow—Methocel Cellulose Ethers Technical Handbook, p. 1-32, Jun. 1997.
Dow—Personal Care Solutions, Cellulosic Thickeners Product Selection Guide, p. 1-2, Feb. 2015.
International Search Report and Written Opinion of the International Searching Authority, PCT/US2016/028827, dated Jul. 28, 2016, 10 pages.
International Search Report and Written Opinion of the International Searching Authority, PCT/US2016/028832, dated Jun. 15, 2016, 10 pages.
International Search Report and Written Opinion of the International Searching Authority, PCT/US2016/028835, dated Jul. 27, 2016, 10 pages.
International Search Report and Written Opinion of the International Searching Authority, PCT/US2016/028840, dated Jul. 27, 2016, 10 pages.
International Search Report and Written Opinion of the International Searching Authority, PCT/US2016/028843, dated Jul. 27, 2016, 10 pages.
International Search Report and Written Opinion of the International Searching Authority, PCT/US2016/028846, dated Jul. 27, 2016, 10 pages.
International Search Report and Written Opinion of the International Searching Authority, PCT/US2018/017738, dated May 9, 2018, 13 pages.
International Search Report and Written Opinion of the International Searching Authority, PCT/US2018/017741, dated May 9, 2018, 12 pages.
All final and non-final office actions for U.S. Appl. No. 17/141,581.
All final and non-final office actions for U.S. Appl. No. 17/176,404.
All final and non-final office actions for U.S. Appl. No. 17/176,417.
All Office Actions, U.S. Appl. No. 15/435,546.

(56) References Cited

OTHER PUBLICATIONS

Getter et al., Ringing Gels and their Fascinating Properties, Colloids and Surfaces, vol. 38,1989, pp. 225-250.
PLUS Search generated internally by the US PTO support staff for this application attached and requested by axaminer AndrewBainbridge using STIC internal services, Feb. 24, 2021 (Year: 2021).
STIC Search Report generated by the US PTO support staff for this application (Chen Haoyi) attached and requested by examinerAndrew Bainbridge, Feb. 25, 2021, 16 pages.

* cited by examiner

SKIN CLEANSING COMPOSITIONS AND METHODS

FIELD OF THE INVENTION

This application relates to a skin cleansing composition with surfactant, perfume, glycerin, and water; and methods relating thereto.

BACKGROUND OF THE INVENTION

Cleansing is an activity that has been done for hundreds of years. Early cleansers were based on either soap chemistry or simple mechanical action in order to remove dirt from the skin, as well as endogenous soils such as sweat, sebum, and body odors. Smelling clean is an important benefit, however, early on, perfume was applied after cleansing as early cleansers were not designed to deposit a consumer preferred amount of perfume on skin. So, the inclusion of large amounts of perfume in a cleansing composition was both wasteful, as it was washed down the drain, and expensive. As skin cleansing compositions have become more complex, providing scent during cleansing and residual scent on the skin after cleansing are expected by users of modern skin cleansers. As such, improved cleansing compositions which can provide scent during cleansing and/or residual scent on the skin are desired, in compositions which retain their effectiveness in cleansing and are easy to dispense and spread on the skin.

SUMMARY OF THE INVENTION

A skin cleansing composition, comprising: from about 20% to about 40%, by weight of the composition, of surfactant; from about 20% to about 40%, by weight of the composition, of glycerin; from about 4% to about 15%, by weight of the composition, of perfume; and water, wherein at least a portion of the composition is in a lamellar phase.

This and other combinations will be more fully understood in light of the detailed description below.

DETAILED DESCRIPTION OF THE INVENTION

Definitions

As used herein, the following terms shall have the meaning specified thereafter:

"Cleansing composition" refers to compositions intended for topical application to the skin for cleansing.

"Concentrate/concentrated" as used herein with respect to a cleansing composition refers to a composition where the weight percentage of surfactant relative to the total composition is greater than about 15%.

"Gel" refers to a material or composition that does not flow under its own weight and has a G' greater than about 25 Pa at 1 Hz in an oscillatory rheology test.

"Micelle" as used herein refers to a structure comprising individual surfactant molecules aggregated to form a hydrophobic core region with externally facing polar head groups in equilibrium with surfactant monomers in a polar phase, having a characteristic dimension that is a single digit multiple of the surfactant length, i.e., generally less than about 10 nm in diameter.

"Microemulsion" as used herein refers to a thermodynamically stable isotropic mixture of oil, surfactant, and water comprising an interior hydrophobic core, having a size greater than about 10 nm diameter.

"Perfume" refers to a mixture of volatile organic oils having a pleasant aroma wherein the perfume components have individual molecular weights between about 75 and 400 Daltons.

"Rinse-off" means the intended product usage includes application to skin followed by rinsing and/or wiping the product from the skin within a few seconds to minutes of the application step. The product is generally applied and rinsed in the same usage event, for example, a shower.

Modern consumers of cleansing compositions expect the composition to provide scent both during use and to have residual scent on the skin after use, making perfume an important component of cleansing compositions. Perfume is also an important component of many skin cleansers to mask the base odor of cleansing ingredients, which can be unpleasant.

Perfume is composed of mostly hydrophobic oil, whereas skin cleansers generally have an aqueous, continuous phase which provides essentially no ability to carry perfume. It is desirable to provide perfume in a soluble form in a liquid skin cleanser, since insoluble phases of any kind can lead to instability problems in the composition. Perfume is therefore generally solubilized within the surfactant component of cleansers, such as micelles, lamellar structures, vesicles and the like. Surfactant structures of all kinds contain hydrophobic regions due to the aggregation of surfactant tails, which are able to solubilize significant quantities of perfume oil. Perfume generally exists within the surfactant tails as a molecular solution due to the interaction of the perfume with the surfactant tails, not as a colloidal structure such as an emulsion droplet, which is not thermodynamically stable.

A problem exists in providing perfume scent during use and residual scent to the skin from skin cleansers. Well known physical laws govern the relationship between perfume in the air in equilibrium with perfume solubilized in a micelle or other environment. This relationship is defined by the mole fraction of perfume in the soluble environment, generally the micelle. Micelles are common features of skin cleansers since even non-micellar surfactant generally becomes micelles during the dilution experienced while cleansing.

Since the perfume concentration in a skin cleanser is generally only 25% or less on a molar basis in the surfactant micelle, the vapor pressure of each perfume molecule can be reduced by 75% or even more, due to its solubilization in the micelle. The desire to deliver perfume to the skin suffers from a similar fate during cleansing. Perfume molecules can diffuse, or partition into the skin during cleansing. The driving force to do so is the thermodynamic activity coefficient gradient for the perfume molecules. While a pure perfume applied to the skin, having a high activity coefficient, can partition quickly into skin, perfume located in a surfactant micelle proximal to the skin suffers from an activity coefficient reduction (75% or more) due to micellar solubilization. Therefore most perfume in cleansing compositions (between 50-90%) generally is washed away during rinsing before it can partition into the skin or bloom into the headspace. The result is the skin retains no or very little scent and only for a short duration after a typical cleansing event. Thus, delivery of perfume to the air and to the skin during cleansing is inefficient and therefore expensive.

Overcoming these technical constraints in order to increase perfume delivery to the skin and the bloom of perfume during a cleansing event is not simply a matter of adjusting formula components at increased cost. Natural limits exist related to factors such as solubility. For example, increasing perfume in a cleansing composition is not only costly, but is also unfeasible considering the abundance of perfume can become insoluble in the surfactant composition, leading to instability. At some point, the amount of perfume exceeds the capacity of the micelles and the composition is no longer transparent, a consumer desirable quality, and the viscosity is reduced. To combat low viscosity and lack of transparency, more surfactant can be added. This approach often results in a composition that is costly to make. In addition, increasing the surfactant level reduces the efficiency of perfume delivery to the skin so that even more perfume is required to achieve the same result. Compositions with acceptable viscosity often require as much as 15 wt % or even 18 wt % surfactant when 2 wt % or more perfume is used.

Various means to overcome this problem have been suggested. Perfume microcapsules have been developed to encapsulate perfume and protect it from contact with surfactant. However, only a limited number of perfume molecules are stable in perfume microcapsules; and the perfume microcapsule itself must then be delivered to the skin and, later, mechanically crushed by the consumer in order to release the perfume. Most perfume microcapsules are themselves washed down the drain during cleansing, affording little benefit.

Additionally, cleansing compositions have been formulated as micelles. Surfactants have a critical micelle concentration, or CMC, at which they aggregate. Below the CMC surfactant exists as monomers in solution. It has been suggested that dilution to below the CMC can release perfume to increase bloom. The problem with this approach is the CMC is very low, often about 100 ppm for cleansing surfactant mixtures (i.e., 0.01 wt. %, a dilution of more than 500-fold from an original composition). Thus, the CMC occurs at concentrations not relevant to cleansing nor rinsing the body. During rinsing, the CMC is reached only at the very end of cleansing, by which time nearly all the cleansing components have already been washed down the drain in the form of micelles, carrying the perfume with them. Relevant dilutions during cleansing are less than 10-fold, especially less than 5-fold, during which time there is extensive exposure of the wash composition to the body and to the air in the shower, affording both time and opportunity for perfume to bloom and partition to the skin, if it can be removed from the environment of the micelle.

Surprisingly, inventors have discovered skin cleansing compositions can deliver enhanced perfume bloom during cleansing and perfume retention on the skin after cleansing. Without wishing to be limited by theory, the enhanced perfume benefits are believed to result, at least in part, when at least a portion of the perfume in a composition exists within the lamellar phase and the composition has the ability to be diluted into a perfume microemulsion. In the microemulsion form, it is believed most perfume is in a central core region and is not proximal to surfactant hydrocarbon, therefore it is not in a solvent-solute relationship which can reduce perfume activity coefficient. The result is bloom and/or relative bloom is significantly enhanced, sometimes doubled or even tripled or more; and scent of perfume over the skin after wash, can be enhanced by a similar magnitude.

To make a perfume microemulsion upon dilution, sufficiency of perfume, which is the oil component for making a perfume core; the right level surfactant; and polyhydric solvents are believed to be contributing factors. Polyhydric solvents have multiple effects like, reducing the dielectric of the water phase, acting as a solvent for the surfactant head groups, reducing interfacial tension between the aqueous phase and hydrocarbon, and interacting with the perfume in the core. During use of the skin cleansing composition, as the composition is diluted, polyhydric solvents are reduced in concentration, the composition begins to transition into a perfume microemulsion because of the abundance of water added during washing and rinsing. This provides a further benefit to increase perfume activity coefficient by increasing perfume molar concentration in the core. Thus, a sufficient amount of polyhydric solvents in the initial composition will form a microemulsion phase upon dilution which can increase perfume activity during use.

Although inventors have found delivering perfume to the headspace and the skin during cleansing can be improved by a microemulsion, a problem exists in that microemulsions have a very low viscosity, so are difficult to dispense and spread on the skin without running off. Preferred means to provide an acceptable rheology involve the use of surfactants to form elongated micelles without the use of other rheology control agents, which can be wasteful and costly. Surprisingly, inventors have found certain compositions with large relative amounts of hydric solvent can be lamellar prior to cleansing, and upon mixing with water on the skin become diluted to become a microemulsion during cleansing and rinsing. Because of the large volume of dilution water involved in skin cleansing and rinsing, a relatively large amount of a hydric solvent is present in the starting composition to form the microemulsion phase upon dilution. Thus, at the same time, it is desirable for the starting composition to be lamellar, and contain a high level of polyhydric solvent.

Figure 2:
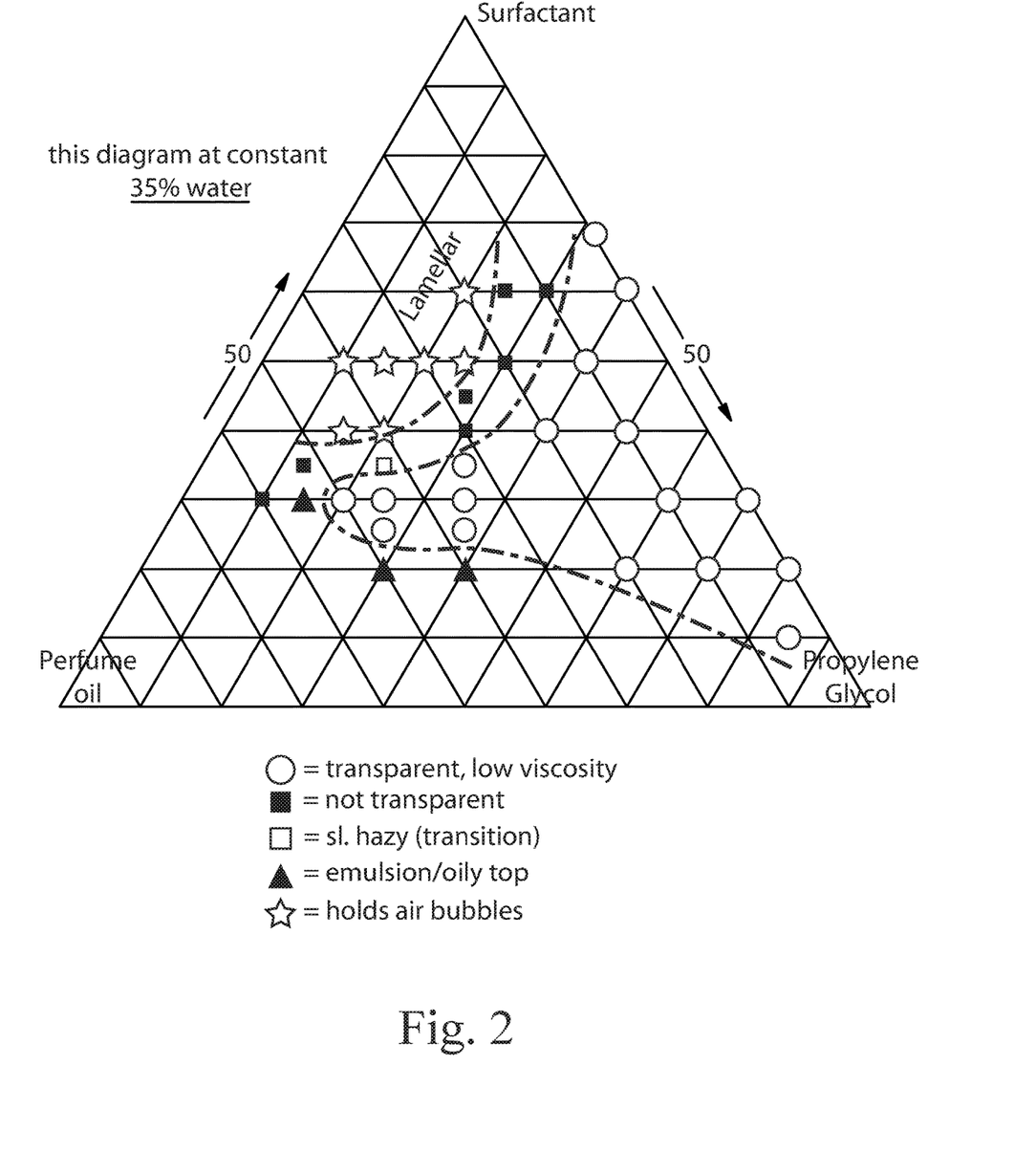
FIG. 2 is a ternary diagram at a constant water percentage of 35% by weight of the composition showing surfactant, propylene glycol, and perfume oil.
Figure 3:
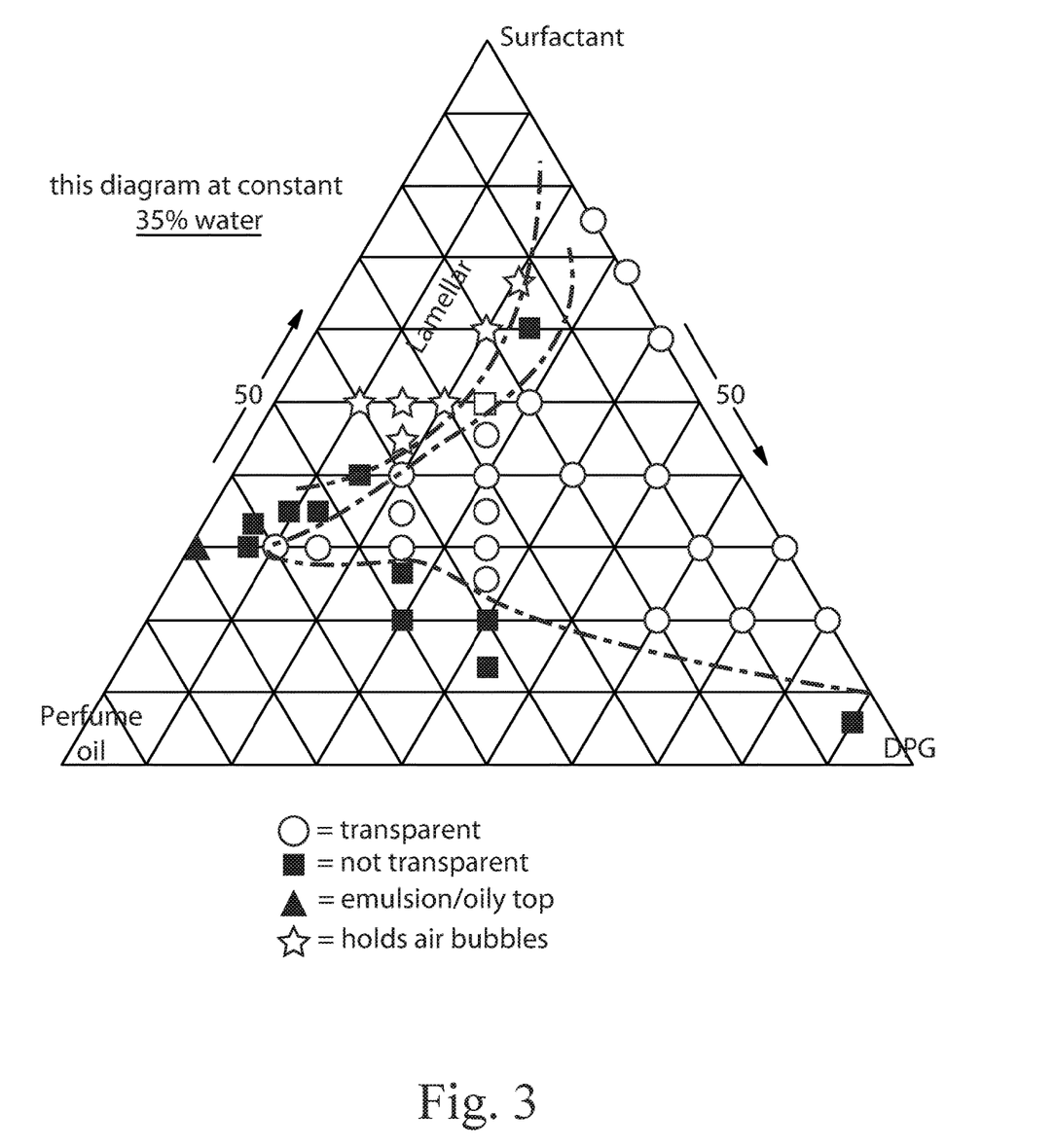
FIG. 3 is a ternary diagram at a constant water percentage of 35% by weight of the composition showing surfactant, dipropylene glycol (DPG), and perfume oil.

Most polyhydric solvents are deleterious to lamellar phase formation, dissolving lamellar structures quite easily. For example, in cleansing compositions having about 30% surfactant and 35% water, no more than about 20% of the polyhydric solvent dipropylene glycol (DPG) can generally be added without dissolving the lamellar phase into a low viscosity fluid phase (see FIG. 3). And, in cleansing compositions having about 20% surfactant and 35% water, no more than about 10% DPG can generally be added without dissolving the lamellar phase (see FIG. 3). This can also be seen in Comparative Examples 1-5 where the compositions go from a gel to a transparent low viscosity fluid as the DPG level is increased from 6.5 wt % to 26 wt %. Moreover, as can be seen in FIG. 2, the ternary phase diagram using propylene glycol shows a structured lamellar phase region extending to only about 25 wt % solvent (as percent of non-aqueous components).

Figure 1:
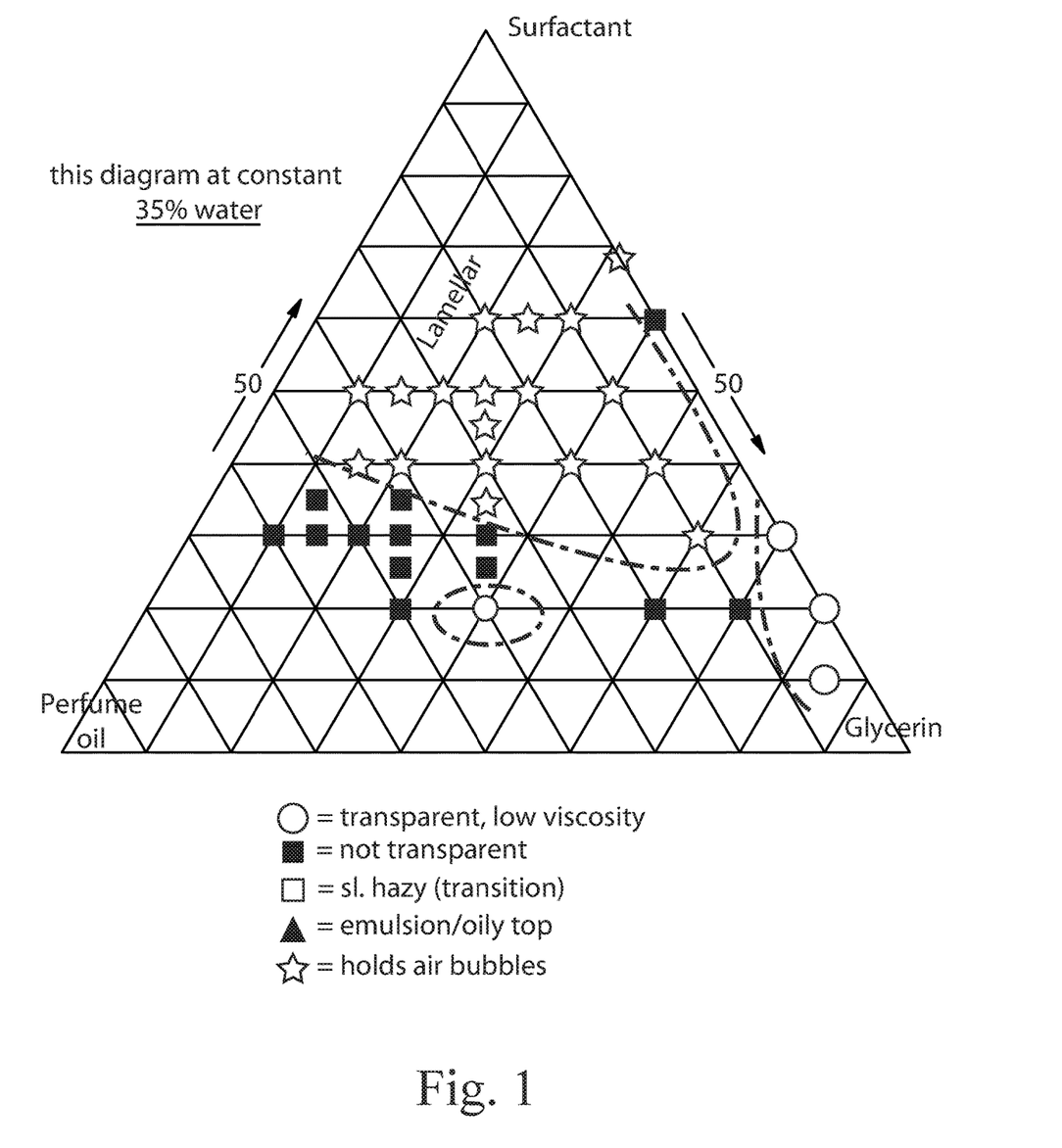
FIG. 1 is a ternary diagram at a constant water percentage of 35% by weight of the composition showing surfactant, glycerin, and perfume oil.

As a polyhydric solvent, inventors have found that glycerin is unique in that it has a broad range over which it can help to create a microemulsion in a skin cleansing composition upon dilution, while it can be added at significantly higher levels than other polyhydric solvents without dissolving the lamellar phase structures in the initial composition. While many solvents can only be added up to an amount of about 10-20%, by weight of the cleansing composition, glycerin continues to be capable of helping the formation of a microemulsion phase up to 20%, or 30%, or even 40%, by weight of the composition (see FIG. 1). This, in turn, allows for additional formulation flexibility.

Solvents, like glycerin, are known to modify the rheological properties of the composition, particularly reducing the viscosity of surfactant compositions. Concentrating a composition into a gel is one way to combat low viscosity to improve dispensing and spreading characteristics. These types of compositions often exhibit a classic x-ray diffraction pattern of a lamellar phase. However, when the level of solvent is greater than about 40%, by weight of the surfactant, it can be difficult to form a structured gel and thus the composition can have a much lower viscosity and is difficult to dispense from conventional body wash packages. This, surprisingly, is not true for glycerin which can accommodate a weight ratio of from about 0.4:1 to about 3:1 surfactant to glycerin. When compositions with an exemplary rheology profile are desired, glycerin can be used to deliver both exemplary rheology and perfume delivery properties. Thus, glycerin can be from about 40% to about 300%, from about 40% to about 200%, from about 60% to about 200%, expressed as a weight percent of the total surfactant.

Compositions may be in a lamellar phase prior to dilution during use, but can be transformed to a perfume microemulsion during use. In some cases, the transformation during dilution to a perfume microemulsion may be brief, within a restricted dilution range, but such range is sufficient to deliver perfume bloom and partitioning into the skin which, once partitioning is effected, it cannot be reversed. Certain microemulsions may be in equilibrium with other phases during dilution of the composition during use. There may be advantages for both the microemulsion and micelle phases to coexist, since micelles may provide superior lather and cleaning properties at the same time the microemulsion may deliver enhanced perfume benefits. Certain analytical measures, such as dynamic light scattering and optical light transmission, can be used as guides, when evaluating microemulsion phases. Additionally, perfume analysis in the headspace is directly relatable to the perfume solvent environment in a composition or a diluted composition, so that gas chromatography-mass spectrometry (GCMS) headspace measures are an indicator of the perfume environment, i.e., the microemulsion phase and the perfume relationship to solvent molecules therein. Well established physical laws govern the relationship between concentration of molecules in the headspace, and the solvent environment of the molecules in solution, e.g., Raoult's Law. Likewise, headspace measurements over the skin after washing are similarly useful, since perfume partitioning into the skin is enhanced by perfume activity coefficient, as previously discussed.

Dynamic Light Scattering is a useful means to detect structures in the size range of microemulsion droplets, and micelles, but the results can be difficult to interpret when more than one structure may be present, such as micelles and a microemulsion both. A bimodal scattering intensity distribution may be present in inventive compositions, suggesting micelles having a diameter generally below 10 nm in equilibrium with larger structures, which are generally greater than about 20 nm which are the perfume microemulsion droplets.

To fit with current consumer habits during body cleansing, a cleansing composition can be in the form of a gel having a structure defined by an elastic modulus, G', a viscous modulus, G", a viscosity, and a shear thinning viscosity ratio as measured by the test methods below. The gel may comprise a lamellar phase, and may or may not have a high concentration of perfume in its headspace prior to being diluted, relative to a micelle composition. In some cases, when the gel has a high perfume concentration in its headspace, it is believed to be in equilibrium with a microemulsion phase, since the gel can evince a characteristic lamellar x-ray diffraction pattern. In other cases, the gel can have a high perfume concentration in the headspace only after dilution water is introduced.

The composition may be concentrated in order to create desirable rheology characteristics, i.e., a gel. Some compositions may be concentrated at least 3-fold relative to conventional body wash, which generally has about 10 wt % surfactant. When the amount of surfactant is greater than about 15 wt % of the composition, the surfactant can be considered to be concentrated and the composition can be considered to be a concentrate. Generally, a composition having about 20 wt % surfactant can be considered about a 2-fold concentrate, a composition having about 30 wt % surfactant a 3-fold concentrate, and so on.

In certain cases, increasing concentration may be preferable because a gel can be created which has both desirable rheology characteristics useful for dispensing, in addition to a sufficiency of glycerin to form the microemulsion phase during dilution of the composition.

Perfume is a benefit agent. Perfume benefits can be realized at different time points for cleansing compositions. Perfume in the package headspace can be important to select a product at the time of purchase. Perfume scent during cleansing, upon introduction of modest amounts of water, such as for example about 3 parts of water per part composition (i.e., a 3:1 dilution ratio), provides a benefit during skin cleansing. During skin cleansing, some perfume can partition into the outer layers of the skin, which can provide a scented skin benefit for a period of time after cleansing, called scent longevity. A governing property for both scent bloom and longevity is the activity coefficient of the perfume molecules, which is a thermodynamic term. Perfume molecules exhibit their maximum vapor pressure only when they are pure. Diluted perfume molecules, whether diluted by surfactant in a micelle, organic solvent, water, etc., exhibit less than their pure vapor pressure. The amount of perfume in a headspace over a composition, diluted composition, or over the skin can be measured analytically, as described in the methods section below. Benefits in initial fragrance intensity, bloom, or longevity can be demonstrated by comparing performance of the compositions before, during, and, or after a skin cleansing event, compared to conventional body wash or shampoo compositions.

In addition to being a benefit agent, perfume is an oil and therefore can be a direct contributor to formation of phases responsible for its activity coefficient (as noted above), and therefore to scent bloom and longevity benefits. As discussed above, perfume oil can generally be added into micelle surfactant mixtures only to about 0.25 weight fraction of the surfactant before it phase separates, whereas diluted cleansing compositions described herein can hold at least 0.5 parts perfume:surfactant, or even 0.75 parts perfume:surfactant, or even more, while remaining transparent, including water diluted compositions. The ability to hold large amounts of perfume in this manner while remaining transparent, isotropic and low viscosity is an indication the diluted composition is a microemulsion phase and is suitable for enhanced perfume benefits.

Perfume can be a carrier for non-scented, hydrophobic additives. Additives which are at least 5 wt %, or at least 10 wt %, or at least 20 wt % miscible with perfume may be employed to increase delivery of the additives to the skin. Any additive which provides a benefit to the skin or the skin environment (e.g., the skin microbiome) may be employed. The additive may provide a direct or indirect benefit, such as antibacterial, antihyperproliferative, anti-inflammatory, chelation, pH regulation, antifungal, antiviral, control of disorders such as acne, atopic dermatitis, eczema, dermatitis, dandruff, antiaging, antiwrinkle, age spot reduction, sunscreen, hydration, moisturization, or any other skin benefit. An advantage of the present compositions is enhanced additive delivery to the skin during cleansing. A further benefit is reduction in activity coefficient of the additive by dilution with perfume is transient due to subsequent evaporation of the perfume on the skin, which increases the thermodynamic activity of the additive after its delivery to the skin.

In addition, some compositions may form microemulsions but perform poorly for lathering and hence cleaning, which are important features for consumers. Compositions which effectively deliver perfume as described above, can also have consumer acceptable lather properties. Lather can be measured in accordance with the Cylinder Method described below. Compositions may have a lather volume of about 300 mL, about 400 mL, about 500 mL, about 600 mL, about 700 mL, or more. Compositions may have a lather density of about 0.03 g/cc, about 0.04 g/cc, about 0.05 g/cc, 0.055 g/cc, 0.06 g/cc, 0.065 g/cc, or more. Compositions may have a lather mass of about 20 g, about 25 g, about 30 g, about 35 g, about 40 g, about 45 g, or more.

In accordance with the above, a cleansing composition comprises a surfactant, glycerin, perfume, and water. Additionally, optional ingredients may also be included as noted herein, for example, preservatives, thickeners, hydrophobic oils, pH modifiers, additives, soap, etc. The cleansing composition is not in the form of a ringing gel. The cleansing composition can be in the form of a microemulsion or may contain a microemulsion phase. At least a portion of the cleansing composition may become a microemulsion upon dilution with water of about 2:1 or 3:1 by weight (water:composition) to about 10:1 by weight (water:composition). The skin cleansing composition may be a rinse-off composition.

A. Surfactant

A skin cleansing composition includes surfactant. Surfactants can provide a cleaning benefit, lather properties, and rheology properties to the compositions. The surfactant may be a single surfactant or a combination of multiple surfactants. The surfactant may include a first surfactant and a cosurfactant. In addition, a surfactant may be branched, linear, or a combination thereof. A composition may comprise from about 20% to about 40%, from about 20% to about 38%, from about 22% to about 35%, or from about 22% to about 30%, by weight of the composition, of total surfactant. The total weight percentages of surfactant mentioned previously in the composition include primary surfactant and any cosurfactant.

The primary surfactant may be anionic. The cleansing composition may include a primary surfactant at a level of from about 15% to about 38%, from about 15% to about 35%, or from about 17% to about 30%, by weight of the composition.

The anionic surfactant can be linear or branched. The anionic surfactant may contain any counter ion such as sodium, potassium, ammonium, triethanolamine, etc. The hydrocarbon chain can be an olefin or be branched or linear or cyclic, such as alkyl benzenes, and generally has between 10 and 20 carbons or 12 to 16 carbons. The anionic surfactant can comprise ethylene oxide groups, such as one EO, or two EO, or three EO, e.g., and can be a sulfate, sulfonate or carboxylate, including acidic sulfonates such as sulfosuccinates. The anionic, for example, can have less than 3.5 EO groups.

Suitable anionic surfactants can include, for example, sodium trideceth-n sulfate and sodium laureth-n sulfate. These materials can have varying levels of ethoxylation. Thus, the levels of ethoxylation are represented by an (n), for example, sodium trideceth-n sulfate. n can range from about 0.5 to about 5. Some exemplary anionic surfactants are sodium trideceth-2 sulfate, sodium trideceth-3 sulfate, sodium laureth-1 sulfate, sodium laureth-2 sulfate, sodium laureth-3 sulfate, sodium paraffin sulfonate, sodium pareth sulfate, or combinations thereof. The anionic surfactant can be a branched surfactant comprising sodium trideceth-2 sulfate, sodium trideceth-3 sulfate, or a combination thereof. In one example, the cleansing composition comprises from about 15% to about 38%, or from about 17% to about 30%, by weight of the composition, of sodium trideceth-2 sulfate.

The cleansing composition may include from about 2% to about 10%, from about 2.5% to about 10%, or from about 2.5% to about 5%, by weight of the composition, of a cosurfactant. The cosurfactant may be, for example, zwitterionic surfactant, amphoteric surfactant, nonionic surfactant, or a combination thereof. Suitable amphoteric or zwitterionic surfactants can include those described in U.S. Pat. Nos. 5,104,646 and 5,106,609.

Additional amphoteric detersive surfactants suitable for use in the cleansing compositions can include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic surfactants suitable for use in the cleansing compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include a betaine, like an alkyl betaine or alkyl amidopropyl betaine, like cocamidopropyl betaine.

Nonionic surfactants suitable for use can include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof. Some exemplary nonionic surfactants can include cocamide monoethanolamine, decyl glucoside, or a combination thereof.

As noted above, the cosurfactant can include a combination of amphoteric, zwitterionic, and nonionic surfactants. One grouping of exemplary cosurfactants includes sodium lauryl amphoacetate, laurylamidopropyl betaine, cocamidopropyl betaine, lauryl betaine, lauryl amine oxide, or a combination thereof.

B. Perfume

A cleansing composition includes a perfume. A composition may comprise from about 4% to about 20%, from about 4% to about 15%, from about 4% to about 13%, about 4% to about 10%, from about 5% to about 12%, from about 5% to about 10%, from about 6% to about 15%, or from about 6% to about 10%, by weight of the composition, of perfume.

Certain perfume features may also impact perfume benefits, such as the proportion of perfume molecules within a volatility or molecular weight range. In general, Kovats Index (KI) is a useful parameter to differentiate perfume molecules. Perfume molecules having KI less than 1100 can be considered high blooming molecules; those having KI greater than 1400 can be considered high skin partitioning molecules; and those between (KI of 1100-1400) can be considered middle perfume notes which generally favor neither bloom nor skin partitioning, but contribute to some extent in both.

C. Glycerin

A cleansing composition includes glycerin. A cleansing composition may comprise from about 20% to about 40%, from about 22% to about 38%, from about 22% to about 37%, or from about 23% to about 35%, by weight of the composition, of glycerin.

D. Water

A cleansing composition includes water. Water may come in with other components or may be added as free water. A cleansing composition may comprise from about 2% to about 66%, from about 5% to about 66%, from about 10% to about 60%, from about 15% to about 55%, or from about 25% to about 50%, by weight of the composition, of water.

E. Rheology—Viscoelasticity and Viscosity

The rheological properties of cleansing compositions can be characterized by viscoelastic parameters and a viscosity. The rheology of a cleansing composition can be defined by its G' and G" values, relating to the composition's structure. G' and G" are measured in accordance with the rheological properties method discussed herein. G' and G" describe a cleansing compositions elastic and viscous response to applied stress, characterizing how the material acts when dispensed from a bottle, sitting on the consumers implement or hand, and how a product spreads on application. It also impacts a consumer's perception of the product, for instance products with low G' values flow too readily in use and are associated in consumer perception and can be perceived as dilute. Conversely products with a high G' are associated in consumer perception with concentrated personal cleansing products. The cleansing composition may have a G' at about 1 Hz of about 25 Pa to about 5000 Pa; from about 50 Pa to about 2500 Pa, from about 75 Pa to about 1200 Pa, from about 100 Pa to about 1500 Pa, or from about 150 Pa to about 1000 Pa. The cleansing composition may have a G" at about 1 Hz of about 18 Pa to about 250 Pa; from about 18 Pa to about 225 Pa, or from about 20 Pa to about 225 Pa.

In addition, the cleansing composition should have a viscosity sufficient to allow it to be dispensed from a package onto an implement or directly onto the skin. The viscosity of a cleansing composition can be measured in accordance with the rheological properties method discussed herein. The cleansing composition may have a viscosity at about 0.10 l/sec of about 20 PaS to about 1000 PaS, from about 30 PaS to about 500 PaS, or from about 40 PaS to about 300 PaS. The cleansing composition may have a viscosity at about 10 l/sec of about 1 PaS to about 100 PaS; from about 1 PaS to about 30 PaS, from about 1 PaS to about 15 PaS, or from about 1 PaS to about 10 PaS.

Compositions can also be highly shear thinning, having a viscosity ratio of less than about 0.20, or 0.10, or even less than 0.05, which is the ratio of the viscosity at 10 l/sec divided by the viscosity at 0.10 l/sec.

F. Preservatives

Liquid cleansing compositions often have a high water activity (i.e. about 0.95 or more). Water activity describes the availability of water within a composition to support various chemical and biological processes requiring water. Compositions with high water activity can allow growth of microorganisms and therefore generally utilize preservatives. For example, bacteria can grow at a water activity of about 0.90 or above and fungus can grow at a water activity of about 0.70 or above. Below these water activities, microorganisms generally dehydrate and die.

The cleansing compositions as noted herein can have a low water activity, less than about 0.90. This low water activity allows the compositions to naturally resist the growth of microorganisms and thus utilize minimal or even no, preservative. In addition, the use of high levels (5 wt. % or more) of glycols, like glycerin, can also help to prevent the growth of microorganisms and further support a composition which needs minimal or even no, preservative.

G. Hydrophobic Oils

The cleansing composition may comprise a hydrophobic oil. Hydrophobic oil can help form a microemulsion phase due to low solubility in the palisade layer of micelles, to further enhance bloom and deposition on skin. The cleansing composition may comprise from about 0% to about 25%, from about 2% to about 20%, or from about 3% to about 15% by weight of the composition, of a hydrophobic oil. Exemplary hydrophobic oils can include, for example, isopropyl myristate, isostearyl isostearate, behenyl behenate, triglycerides such as soybean oil, hydrocarbon such as mineral oil, or combinations thereof.

H. Additives

The cleansing composition may comprise an additive. Additives are materials that are at least partially soluble in the perfume. It is believed that additives which are at least partially soluble in the perfume will also see a deposition benefit. Additives which are at least 5 wt %, or at least 10 wt %, or at least 20 wt % miscible with perfume may be employed to increase delivery of the additives to the skin or hair. Some examples of classes of material that can be soluble in the perfume are skin actives, vitamins, antibacterials, antifungals, chelants, or combinations thereof.

Examples of skin actives which can be included are sunscreens; anti-acne medicaments; antioxidants; skin soothing agents, skin healing agents; essential oils, skin sensates, anti-wrinkle medicaments, or mixtures thereof. Some examples of skin soothing agents can include, for example, aloe vera, allantoin, bisabolol, dipotassium glycyrrhizinate, or combinations thereof.

Examples of vitamins which can be included are Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, tocopherol nicotinate, etc.), Vitamin K (e.g., phytonadione, menadione, phthiocol, etc.), or combinations thereof.

Examples of antibacterials and/or antifungals which can be included are glycolic acid, lactic acid, phytic acid, N-acetyl-L-cysteine, phenoxyethanol, phenoxypropanol, phenoxyisopropanol, zinc pyrithione, octopirox (piroctone olamine), climbazole, ketoconazole, thymol, terpineol, essential oils, or combinations thereof.

Examples of chelants which can be included are 2-aminoethyl phosphoric acid (AEP), N-phosphonomethyl aminodiacetic acid (PMIDA), 1-hydroxyethane-1,1-diphosphonic acid (HEDP), amino tris(methylene phosphonic acid) (ATMP), ethylenediamine tetra(methylene phosphonic acid) (EDTMP), diethylenetriamine penta(methylene phosphonic acid) (DTPMP), phytic acid, nitrilotrimethylene phosphonic acid (NIP), 2-hydroxypyridine oxide (HPNO), or combinations thereof.

The cleansing composition may comprise from about 1% to about 20%, from about 2% to about 10%, or from about 3% to about 8%, by weight of the composition, of an additive.

I. Soap

Cleansing compositions as described herein may also comprise soap.

J. Packaging

Compositions can be dispensed from a squeezable package with an orifice, such as a conventional body wash or shampoo package. The package can be a compact package, i.e., contain less than about 250 ml, or 200 ml, or 150 ml of volume to signal the contents are concentrated. The shear thinning compositions can be dispensed from a package with a slit valve orifice or other flexible orifice, which is generally cut from a silicone elastomeric material and inserted into an orifice housing. Compositions can also be dispensed from liquid pump packages.

K. Methods

In addition to the compositional elements and parameters noted above, it is believed there are also some inventive benefits and/or uses to the compositions which are set out as methods below. For the sake of brevity, all of the compositional elements and parameters noted above are not repeated herein, but can be used within the methods where relevant.

A method of enhancing in-vitro bloom of a skin cleansing composition, comprising, combining: from about 20% to about 40%, by weight of the composition, of surfactant; from about 20% to about 40%, by weight of the composition, of glycerin; from about 4% to about 15%, by weight of the composition, of perfume; and water, wherein at least a portion of the composition is lamellar.

A method of enhancing fragrance longevity on skin, comprising, combining: from about 20% to about 40%, by weight of the composition, of surfactant; from about 20% to about 40%, by weight of the composition, of glycerin; from about 4% to about 15%, by weight of the composition, of perfume; and water, wherein at least a portion of the composition is lamellar.

Exemplary Combinations

A. A skin cleansing composition, comprising: from about 20% to about 40%, by weight of the composition, of total surfactant; from about 20% to about 40%, by weight of the composition, of glycerin; from about 4% to about 15%, by weight of the composition, of perfume; and water.

B. The skin cleansing composition of paragraph A, wherein the total surfactant is from about 20% to about 38%, from about 22% to about 35%, or from about 22% to about 30%, by weight of the composition.

C. The skin cleansing composition of any of paragraphs A-B, wherein the surfactant comprises from about 15% to about 38%, from about 15% to about 35%, or from about 17% to about 30%, by weight of the composition, of an anionic surfactant.

D. The skin cleansing composition of any of paragraphs A-C, wherein the surfactant comprises from about 2% to about 10%, from about 2.5% to about 10%, or from about 2.5% to about 5%, by weight of the composition, of a cosurfactant.

E. The skin cleansing composition of any of paragraphs C-D, wherein the anionic surfactant is branched.

F. The skin cleansing composition of any of paragraphs D-E, wherein the cosurfactant is zwitterionic.

G. The skin cleansing composition of any of paragraphs D-F, wherein the cosurfactant comprises a betaine.

H. The skin cleansing composition of any of paragraphs D-G, wherein the cosurfactant comprises cocamidopropyl betaine, laurylamidopropyl betaine, or a combination thereof.

I. The skin cleansing composition of any of paragraphs B-H, wherein the anionic surfactant comprises sodium trideceth-2 sulfate, sodium trideceth-3 sulfate, sodium laureth-1 sulfate, sodium laureth-2 sulfate, sodium laureth-3 sulfate, or a combination thereof.

J. The skin cleansing composition of any of paragraphs A-I, wherein the composition is a microemulsion or contains a microemulsion phase.

K. The skin cleansing composition of any of paragraphs A-J, wherein the composition is not a ringing gel.

L. The skin cleansing composition of any of paragraphs A-J, wherein at least a portion of the composition becomes a microemulsion upon dilution with water of about 3:1 by weight (water:composition) to about 10:1 by weight (water:composition).

M. The skin cleansing composition of any of paragraphs A-L, wherein the glycerin is from about 22% to about 38%, from about 22% to about 37%, or from about 23% to about 35%, by weight of the composition.

N. The skin cleansing composition of any of paragraphs A-M, wherein the perfume is from about 4% to about 13%, from about 5% to about 12%, from about 5% to about 10%, from about 6% to about 15%, or from about 6% to about 10%, by weight of the composition.

O. The skin cleansing composition of any of paragraphs A-O, wherein the anionic surfactant comprises sodium trideceth-2 sulfate.

P. The skin cleansing composition of any of paragraphs D-O, wherein the cosurfactant comprises cocamidopropyl betaine.

Q. The skin cleansing composition of any of paragraphs A-P, wherein the composition is a gel.

R. The skin cleansing composition of any of paragraphs A-P, wherein the composition has a G' at about 1 Hz of about 25 Pa to about 5000 Pa; from about 50 Pa to about 2500 Pa, from about 75 Pa to about 1200 Pa, from about 100 Pa to about 1500 Pa, or from about 150 Pa to about 1000 Pa.

S. The skin cleansing composition of any of paragraphs A-R, wherein the composition has a G" at about 1 Hz of about 18 Pa to about 250 Pa; from about 18 Pa to about 225 Pa, or from about 20 Pa to about 225 Pa.

T. The skin cleansing composition of any of paragraphs A-S, wherein at least a portion of the composition is lamellar.

U. Use of the composition of any of paragraphs A-T for enhanced perfume delivery to skin.

V. Use of the composition of any of paragraphs A-T to enhance fragrance of a skin cleansing composition on skin.

EXAMPLES

| | A | B | C | D | E |
|---|---|---|---|---|---|
| sodium trideceth-2 sulfate | 28.86 | 18.1 | 18.71 | 18.72 | 17.41 |
| cocamidopropyl betaine | 4.29 | 2.69 | 2.78 | 2.78 | 2.59 |
| glycerin | 22.75 | 38.35 | 22.0 | 24.5 | 25.0 |
| perfume | 9.1 | 5.85 | 6.5 | 4 | 5 |
| citric acid | 0.3 | 0.3 | 0.3 | 0.3 | 0.3 |
| water | qs | qs | qs | qs | qs |
| active surfactant | 33.2 | 20.8 | 21.5 | 21.5 | 20 |
| dose (g/use) | 3.32 | 5.29 | 5.12 | 5.12 | 5.5 |
| mg perfume/dose | 302 | 309 | 333 | 205 | 275 |
| observations | rigid gel | rigid gel | rigid gel | flowable gel | soft gel |
| G' at 1 Hz | 1,778 | 211 | 511 | 76 | 155 |
| G" at 1 Hz | 217 | 18.6 | 25.8 | 19.9 | 26.2 |
| tan delta | .122 | .088 | .050 | .262 | .169 |
| viscosity at 0.01 1/sec (Pa-s) | 3197 | 823 | 1561 | 85.1 | 115.4 |
| viscosity at 10 1/sec (Pa-s) | 49.2 | 13.8 | 15.2 | 1.77 | 2.55 |

| EXAMPLE | F | G | H | I | J | K | L |
|---|---|---|---|---|---|---|---|
| sodium trideceth-2 sulfate | 17.39 | 22.44 | 28.05 | 33.66 | 33.66 | 28.05 | 22.44 |
| cocamidopropyl betaine | 2.76 | 3.56 | 4.45 | 5.34 | 5.34 | 4.45 | 3.56 |
| glycerin | 38.35 | 32.5 | 26.0 | 19.5 | 13.0 | 13.0 | 26.0 |
| dipropylene glycol | 0 | 0 | 0 | 0 | 0 | 0 | 0 |
| perfume | 6.5 | 6.5 | 6.5 | 6.5 | 13 | 19.5 | 13 |
| water | 35.0 | 35.0 | 35.0 | 35.0 | 35.0 | 35.0 | 35.0 |
| Total | 100.0 | 100.0 | 100.0 | 100.0 | 100.0 | 100.0 | 100.0 |
| observed at 24 hr | gel | gel | gel | gel | gel | gel | gel |
| G'/Pa (at 1 Hz) | 341 | 500 | 545 | 858 | 975 | 373 | 352 |
| G"/Pa (at 1 Hz) | 18.4 | 38.1 | 55.7 | 115 | 155.2 | 65.3 | 41.2 |
| tan δ | 0.05 | 0.08 | 0.10 | 0.13 | 0.16 | 0.18 | 0.12 |
| viscosity/Pa*s (at 0.1 1/s) | 210 | 191 | 222 | 288 | 213 | 67 | 117 |
| viscosity/Pa*s (at 1 1/s) | 69 | 39 | 49 | 57 | 42 | 17 | 36 |
| viscosity/Pa*s (at 10 1/s) | 9.8 | 10.9 | 12 | 14.1 | 11.2 | 4.8 | 9.1 |

| EXAMPLE | comparative 1 | comparative 2 | comparative 3 | comparative 4 | comparative 5 |
|---|---|---|---|---|---|
| sodium trideceth-2 sulfate | 28.05 | 28.05 | 33.66 | 28.05 | 33.66 |
| cocamidopropyl betaine | 4.45 | 4.45 | 5.34 | 4.45 | 5.34 |
| glycerin | 0.00 | 0.00 | 0.00 | 0.00 | 0.00 |
| dipropylene glycol | 26.0 | 16.25 | 13.0 | 13.0 | 6.50 |
| perfume | 6.5 | 16.25 | 13 | 19.5 | 19.5 |
| water | 35.0 | 35.0 | 35.0 | 35.0 | 35.0 |
| Total | 100.0 | 100.0 | 100.0 | 100.0 | 100.0 |
| observed at 24 hr | transparent low viscosity liquid | hazy low viscosity liquid | gel | gel | gel |
| G'/Pa (at 1 Hz) | 0.0059 | 0.032 | 424 | 70.5 | 1018 |
| G"/Pa (at 1 Hz) | 0.31 | 0.45 | 62.7 | 31.3 | 65.3 |
| tan δ | 52.5 | 14.1 | 0.15 | 0.4 | 0.06 |
| viscosity/Pa*s (at 0.1 1/s) | 0.075 | 0.215 | 100 | 15 | 202 |
| viscosity/Pa*s (at 1 1/s) | 0.054 | 0.094 | 9.7 | 2.3 | 18 |
| viscosity/Pa*s (at 10 1/s) | 0.058 | 0.064 | 1.71 | 0.76 | 3.4 |

Examples A-L and Comparative Examples 1-5 are prepared by weighing the components together into a Speedmixer pot, stirring by hand briefly to homogenize the fluids, and then speedmixing for 60 seconds at 2750 rpm.

Test Methods a) G' and G" Test Method

To measure the viscoelastic properties of a personal care composition, the viscous (G") and elastic (G') moduli, use a rheometer such as a AR G2 Rheometer (TA Instruments, DE, USA) with 1 degree cone upper geometry with a diameter of 40 mm and flat plate lower geometry with Peltier heating/cooling to control temperature. Place approximately 1 gram of personal care composition onto the lower test geometry and lower the upper geometry into position, lock the geometry and wipe away excess composition to create an even surface around the edge of the geometry. Conduct the oscillatory test over frequency range of 0.01 to 100 Hz, collecting 5 data points per decade, using a constant oscillatory stress of 0.5968 Pa and a temperature of 25° C. The tan delta is calculated as the ratio of G"/G'.

Record the G' and G" (Pa) at a frequency of 1 Hz.

b) Viscosity Method

To measure the viscosity of a personal care composition use a rheometer such as an AR G2 controlled stress Rheometer (TA Instruments, DE, USA) equipped with 1 degree cone upper geometry with a diameter of 40 mm and flat plate lower geometry equipped with Peltier heating/cooling to control temperature. Pipette approximately 1 gram of personal care composition onto the lower test geometry and lower the upper geometry into position, wipe away any excess composition to create an even surface around the edge of the geometry. Conduct a continuous flow test at 25° C., controlling the shear rate from 0.01 to 100 1/sec over a time period of 3 minutes, running the test in log mode and collecting 15 points per decade. Record the viscosity (Pa*s) at the shear rates of 0.10 1/sec, 1 1/sec, and 10 1/sec.

c) Cylinder Method

Lather can be measured in accordance with the Cylinder Method. Lather volume is measured using a graduated cylinder and a rotating mechanical apparatus. A 1,000 ml graduated cylinder is used which is marked in 10 ml increments, has a height of 14.5 inches at the 1,000 ml mark from the inside of its base, and has a neck at its top fitted for a plastic insert cap (for example, Pyrex No. 2982). Moderately hard water is prepared with 1.5:1 ion ratio Ca/Mg by dissolving 1.14 grams calcium chloride dihydrate and 1.73 grams magnesium chloride hexahydrate into one U.S. gallon distilled water. The water is maintained at between 105-110° F. The graduated cylinder is heated to about the same temperature by flushing with excess tap water at the same temperature for about 15 seconds, then drying it outside and shaking briefly upside down to dry the interior. 100.0 grams of the moderately hard water at the indicated temperature is weighed directly into the graduated cylinder. The cylinder is clamped in a mechanical rotating device, which clamps the cylinder vertically with an axis of rotation that transects the center of the graduated cylinder. Using a 3- or 4-place metric balance, invert the plastic cap for the graduated cylinder onto the balance pan and weigh 0.500 grams of composition (for compositions less than 19% surfactant) to within 4 milligrams accuracy, using a holder to keep the cap level. When the surfactant level is 40% or greater, use 125 mg of composition (500 g/4). When it is between 30% and 39%, use 135 mg of composition, and when it is between 20% and 29% use 250 mg and for 19 wt % and below use 500 mg. Insert the cap into the graduated cylinder neck while being careful that all composition is now in the space in the cylinder interior. For compositions with very low viscosity which will not remain on the cap surface, 500 mg composition can be added directly to the graduated cylinder. Rotate the cylinder for 25 complete revolutions at a rate of about 10 revolutions per 18 seconds to create a lather and stop in a level, vertical position. When the cylinder stops in a vertical position, start a digital stopwatch. Observing the water draining at the bottom, record the time to the nearest second when the water height measures 50 cc, then 60 cc, then 70 cc and so on until at least 90 cc has drained. Measure and record the total height of the foam in the column interior, which is the lather volume. If the top surface of the lather is uneven, the lowest height at which it is possible to see halfway across the graduated cylinder is the lather volume (ml). If the lather is coarse such that a single or only a few foam cells ("bubbles") reach across the entire cylinder, the height at which at least about 10 foam cells are required to fill the space is the lather volume, also in ml up from the base. When measuring the lather height, bubbles that are larger than about 1 inch across at the top surface are considered free air and not lather. The measurement is repeated and at least three results averaged to obtain the lather volume. In a spreadsheet, calculate the lather density at each observed time point as the volume of foam (total height minus water height) divided by the weight of the foam (100.5 grams minus the weight of water observed, using a density of 1.00 g/cc for water). Fit the 3 time points closest to (ideally, also bracketing) 20 seconds to a $2^{nd}$ order polynomial equation. Solve the equation for the lather density at 20 seconds, which is the lather density of the composition. Multiply the lather volume by the lather density to obtain the lather mass, in grams.

The entire process should take less than about 3 minutes in order to maintain desired temperature.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin cleansing composition, consisting of:
  a. from about 26% to about 40%, by weight of the composition, of surfactant comprising a zwitterionic co-surfactant and a branched anionic surfactant;

b. from 20% to about 40%, by weight of the composition, of glycerin;

c. greater than 15% to about 20%, by weight of the composition, of perfume;

d. water;

e. optionally a preservative, thickener, hydrophobic oil, additive, soap, pH modifier, additional hydric solvent, an additional surfactant, solvent, dye, acid, sodium chloride, or a combination thereof;

wherein the composition predominantly comprises a lamellar structures comprising at least a portion of the branched anionic surfactant;

wherein the composition forms a microemulsion comprising at least a portion of the perfume upon aqueous dilution;

wherein the composition comprises a weight ratio of surfactant to glycerin of from about 0.4:1 to about 3:1.

2. The skin cleansing composition of claim 1, wherein the surfactant comprises from about 15% to about 38%, by weight of the composition, of the branched anionic surfactant.

3. The skin cleansing composition of claim 2, wherein the surfactant comprises from about 2% to about 10%, by weight of the composition, of the zwitterionic cosurfactant.

4. The skin cleansing composition of claim 3, wherein the zwitterionic cosurfactant comprises cocamidopropyl betaine, laurylamidopropyl betaine, or a combination thereof.

5. The skin cleansing composition of claim 2, wherein the branched anionic surfactant comprises sodium trideceth-n sulfate, wherein n is from about 0.5 to about 3.

6. The skin cleansing composition of claim 1, wherein the composition is not a ringing gel.

7. The skin cleansing composition of claim 1, wherein at least a portion of the composition forms the microemulsion upon dilution with water of about 3:1 by weight (water:composition) to about 10:1 by weight (water:composition).

8. The skin cleansing composition of claim 2, wherein the branched anionic surfactant is from about 17% to about 30%, by weight of the composition.

9. The skin cleansing composition of claim 3, wherein the zwitterionic cosurfactant is from about 2.5% to about 5%, by weight of the composition.

10. The skin cleansing composition of claim 9, wherein the glycerin is from about 30% to about 40%, by weight of the composition.

11. The skin cleansing composition of claim 5 wherein the anionic surfactant comprises sodium trideceth-2 sulfate.

12. The skin cleansing composition of claim 11, wherein the zwitterionic cosurfactant comprises cocamidopropyl betaine.

13. The skin cleansing composition of any of claim 12, wherein the composition is in the form of a gel.

14. The skin cleansing composition of claim 1, wherein the composition has a G' at about 1 Hz of about 25 Pa to about 5000 Pa.

15. The skin cleansing composition of claim 1, wherein the composition has a G" at about 1 Hz of about 18 Pa to about 250 Pa.

16. The skin cleansing composition of claim 1, wherein the composition does not contain a micellar phase prior to dilution.

17. The skin cleansing composition of claim 1, wherein the composition comprises from about 30% to about 40%, by weight of the composition, of the surfactant.

18. A skin cleansing composition, consisting of:

a. from about 17% to about 30%, by weight of the composition, sodium trideceth-n sulfate, wherein n is from about 0.5 to about 3;

b. from about 2% to about 5%, by weight of the composition, cosurfactant selected from the group consisting of cocamidopropyl betaine, laurylamidopropyl betaine, or a combination thereof;

c. up to 20%, by weight of the composition, glycerin;

d. greater than 15% to about 20%, by weight of the composition, of perfume;

e. water;

f. optionally a preservative, thickener, hydrophobic oil, additive, soap, pH modifier, additional hydric solvent, an additional surfactant, solvent, dye, acid, sodium chloride, or a combination thereof;

wherein the composition predominantly comprises a lamellar structures comprising at least a portion of the sodium trideceth-n sulfate;

wherein the composition forms a microemulsion comprising at least a portion of the perfume upon aqueous dilution;

wherein the composition comprises a weight ratio of surfactant to glycerin of from about 0.4:1 to about 3:1.

19. A skin cleansing composition, consisting of:

a. from about 15% to about 30%, by weight of the composition, branched anionic surfactant;

b. from about 2% to about 5%, by weight of the composition, zwitterionic cosurfactant;

c. up to 20%, by weight of the composition, glycerin;

d. greater than 15% to about 20%, by weight of the composition, of perfume;

e. from about 35% to about 65%, by weight of the composition, water;

f. optionally a preservative, thickener, hydrophobic oil, additive, soap, pH modifier, additional hydric solvent, an additional surfactant, solvent, dye, acid, sodium chloride, or a combination thereof;

wherein the composition predominantly comprises a lamellar structures comprising at least a portion of the branched anionic surfactant;

wherein the composition forms a microemulsion comprising at least a portion of the perfume upon aqueous dilution;

wherein the composition comprises a weight ratio of surfactant to glycerin of from about 0.4:1 to about 3:1.

* * * * *